US00PP23932P2

(12) United States Plant Patent
Lubbe

(10) Patent No.: US PP23,932 P2
(45) Date of Patent: Sep. 24, 2013

(54) ***SALVIA* PLANT NAMED 'CURLING WAVES'**

(50) Latin Name: ***Salvia* hybrid**
Varietal Denomination: Curling Waves

(75) Inventor: Remy Lubbe, Noordwijkerhout (NL)

(73) Assignee: Holding MZ Partners B.V. (NL)

( * ) Notice: Subject to any disclaimer, the term of this patent is extended or adjusted under 35 U.S.C. 154(b) by 16 days.

(21) Appl. No.: 13/373,209

(22) Filed: Nov. 7, 2011

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Cassandra Bright

(57) ABSTRACT

A new and distinct *Salvia* cultivar named 'CURLING WAVES' is disclosed, characterized by unique foliage color change during Spring from red to green. 'CURLING WAVES' produces blue flowers with white stripes continuously from Spring to Autumn. The new variety is a *Salvia*, normally produced as an outdoor garden or container plant.

2 Drawing Sheets

Latin name of the genus and species: *Salvia* hybrid.
Variety denomination: 'CURLING WAVES'.

BACKGROUND OF THE INVENTION

The new cultivar is a product of a planned breeding program conducted by the inventor, Remy Lubbe, a citizen of the Netherlands. Unnamed, unpatented *Salvia* plants were crossed during the Summer of 2006, at a commercial nursery in Noordwijkerhout, the Netherlands. The new variety was discovered in the Summer of 2007, at the same commercial nursery by the inventor, Remy Lubbe, in a group of seedlings resulting from that crossing. The names and species of the parent varieties are unknown.

Asexual reproduction of the new cultivar 'CURLING WAVES' by vegetative cuttings was first performed at the same commercial greenhouse in Noordwijerhout, the Netherlands during 2008. At least 3 more generations have since been produced, and have shown that the unique features of this cultivar are stable and reproduced true to type on successive generations.

SUMMARY OF THE INVENTION

The cultivar 'CURLING WAVES' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CURLING WAVES' These characteristics in combination distinguish 'CURLING WAVES' as a new and distinct *Salvia* cultivar:

1. Unique foliage color change during Spring from red to green.
2. Bright blue flowers with white stripes.
3. Continuous flowering from Spring to Autumn.

PARENT COMPARISON

Plants of the new cultivar 'CURLING WAVES' are similar to plants of the seed parent, an unknown *Salvia* in most horticultural characteristics. However, plants of the new cultivar are more compact in growth habit, more cold hardy, and produce darker blue flowers than the seed parent.

Plants of the new cultivar 'CURLING WAVE' are similar to plants of the pollen parent, an unknown *Salvia* in most horticultural characteristics. However plants of the new cultivar are more compact in growth habit, more cold hardy, and produce darker blue flowers than the pollen parent.

COMMERCIAL COMPARISONS

Plants of the new cultivar 'CURLING WAVES' can be compared to the unpatented variety *Salvia farinacea* 'Victoria'. Plants of 'CURLING WAVES' are similar to plants of, 'Victoria' in most horticultural characteristics, however, plants of the new cultivar 'CURLING WAVES' are winter hardy, whereas 'Victoria' is not winter hardy Additionally, 'CURLING WAVES' flowers continuously, and produces foliage that changes color in the Spring, characteristics not seen in 'Victoria.'

BRIEF DESCRIPTION OF THE PHOTOGRAPHS

Figure 1:
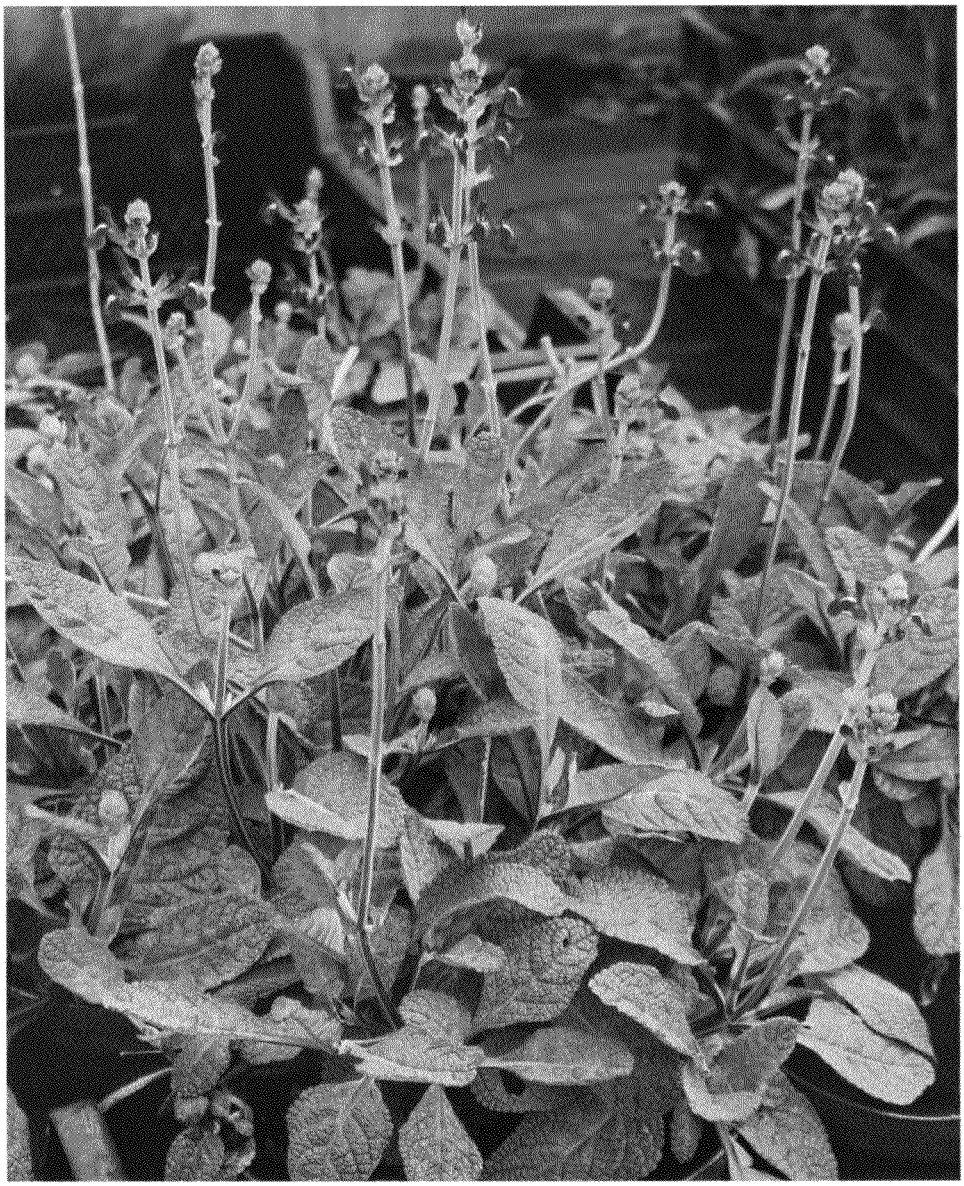

The accompanying photograph in FIG. 1 illustrates in full color typical plant of 'CURLING WAVES' grown outdoors, in a commercial nursery in Noordwijkerhout, the Netherlands.

Figure 2:
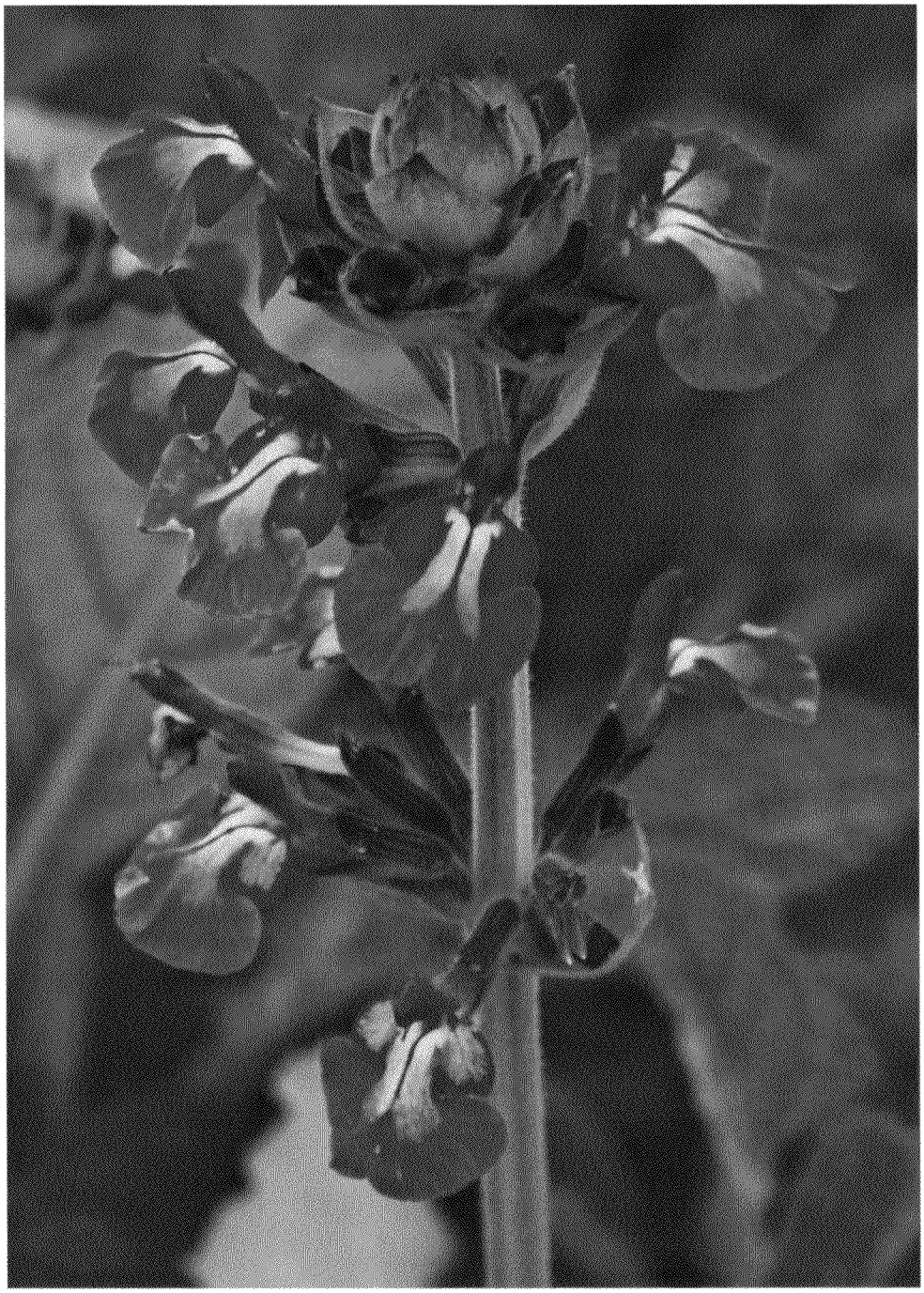

FIG. 2 illustrates in full color a close up of a flower spike from a plant of 'CURLING WAVES'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'CURLING WAVES' plants grown outdoors at a commercial nursery in Noordwijkerhout, the Netherlands. The growing temperature ranged from 0° C. to 28° C., day and night. Measurements and numerical values represent averages of typical plant types.

Botanical classification: *Salvia* hybrid 'CURLING WAVES'.

PROPAGATION

Time to initiate roots: About 10 days at approximately 20° C.
Time to produce a rooted cutting: About 4 weeks at 20° C.

PLANT

Plant spread: Approximately 30 cm.
Growth rate: Rapid.
Length of primary lateral branches: Approximately 50 cm.
Diameter of lateral branches: Approximately 0.3 cm.
Quantity of lateral branches: About 30.
Stem:
- *Color*.—Near RHS Greyed-Red 178 B.
- *Texture/pubescence*.—Pulverulent.

Internode length: Approximately 6 cm.
Age of plant described: Approximately 16 months from a rooted cutting.

FOLIAGE

Leaf:
- *Arrangement*.—Opposite.
- *Quantity*.—Approximately 2 per main branch.
- *Average length*.—Approximately 5 cm.
- *Average width*.—Approximately 2 cm.
- *Shape of blade*.—Ovate.
- *Apex*.—Broadly acute.
- *Base*.—Cuneate.
- *Attachment*.—Stalked.
- *Margin*.—Crenate.
- *Texture of top surface*.—Canescent.
- *Texture of lower surface*.—Canescent.
- *Color*.—Young foliage upper side: Near RHS Greyed-Red 185 A. Young foliage under side: Near RHS Greyed-Red 185 A. Mature foliage upper side: Near RHS Green 139 B. Mature foliage under side: Near RHS Green 138 B.
- *Venation*.—Type: arcuate. Venation color upper side: Near RHS Green 139 B. Venation color under side: Near RHS Green 138 C.
- *Petiole*.—Average Length: Approximately 2.5 cm. Diameter: Approximately 0.2 cm. Color: Near RHS Greyed-Red 178 B.

FLOWER

Natural flowering season: Spring.
Inflorescence type and habit: Glomerule.
Flower longevity on plant: 2 to 3 weeks.
Quantity of flowers: About 15-20 blooming spikes per plant.
Inflorescence size:
- *Diameter*.—Approximately 3-5 cm.
- *Height*.—Approximately 10 cm.

Peduncle:
- *Length*.—0.3 cm.
- *Diameter*.—0.2 cm.
- *Color*.—Near RHS Purple 79 A.
- *Orientation*.—Upright.
- *Strength*.—Strong.

Petals:
- *Petal arrangement*.—Bilabiate.
- *Petal quantity*.—One upper lip, one lower lip.
- *Margin*.—Entire.
- *Apex shape*.—Upper: hooked; lower: two lobed.
- *Length*.—Upper: 7-9 mm; lower: 9-12 mm.
- *Width*.—Upper 3 mm; lower 15 mm.
- *Texture*.—Glabrous.
- *Petaloids*.—None.
- *Color*.—Petals: When opening: Upper surface: Near RHS Violet-Blue 95 B, but more purple, faint stripes near N155A in center. Lower surface: Near RHS Violet-Blue 95 B, but more purple. Fully opened: Upper surface: Near RHS Violet-Blue 95 B, but more purple, faint stripes near N155A in center. Lower surface: Near RHS Violet-Blue 95 B, but more purple.

Bud:
- *Shape*.—Oval.
- *Length*.—0.3 cm.
- *Diameter*.—0.15 cm.
- *Color*.—Near RHS Green 139 C.

Sepals:
- *Shape*.—Fused into tube.
- *Quantity per flower*.—3 to 5 fused into single tube.
- *Length*.—Approximately 6 to 8 mm.
- *Width*.—Approximately 3 mm.
- *Margin*.—Between acute and acuminate.
- *Texture*.—Rough and canescent.
- *Color*.—Near RHS Greyed-Purple N186B with stripes Greyed-Green 191A.

REPRODUCTIVE ORGANS

Stamens:
- *Number*.—2 per flower.
- *Filament length*.—Approximately 0.5 cm.

Anthers:
- *Shape*.—Oval.
- *Length*.—Approximately 0.2 cm.
- *Color*.—Near RHS Yellow 11 A.
- *Pollen*.—Not observed.

Pistil:
- *Number*.—1 per flower.
- *Length*.—Approximately 1.2 cm.
- *Style*.—Length: Approximately 1 cm. Color: Near RHS White 155 C.
- *Stigma*.—Shape: lobed, 2 parted. Color: Near RHS Violet-Blue 92 B.

OTHER CHARACTERISTICS

Seeds and fruits: Not observed to date.
Disease/pest resistance: Neither resistance nor susceptibility to pathogens and pests common to *Salvia* have been observed.
Temperature tolerance: The new variety tolerates temperatures approximately between −15 to 40° C.
Drought tolerance: Established plants can tolerate infrequent Summer watering.

What is claimed is:

1. A new and distinct cultivar of *Salvia* plant named 'CURLING WAVES' as herein illustrated and described.

* * * * *